(12) United States Patent
Orr et al.

(10) Patent No.: US 9,675,300 B2
(45) Date of Patent: Jun. 13, 2017

(54) INTUITIVE PRESENTATION OF VENTILATION EFFECTIVENESS

(75) Inventors: Joseph Allen Orr, Park City, UT (US); Lara Brewer, Bountiful, UT (US); Dwayne Ronald Westenskow, Salt Lake City, UT (US); Matthias Goerges, Vancouver (CA)

(73) Assignee: Koninklijke Philips N.V., Eindhoven (NL)

( * ) Notice: Subject to any disclaimer, the term of this patent is extended or adjusted under 35 U.S.C. 154(b) by 808 days.

(21) Appl. No.: 13/817,464

(22) PCT Filed: Aug. 31, 2011

(86) PCT No.: PCT/IB2011/053814
§ 371 (c)(1),
(2), (4) Date: Feb. 18, 2013

(87) PCT Pub. No.: WO2012/029034
PCT Pub. Date: Mar. 8, 2012

(65) Prior Publication Data
US 2013/0150734 A1 Jun. 13, 2013

Related U.S. Application Data

(60) Provisional application No. 61/379,421, filed on Sep. 2, 2010.

(51) Int. Cl.
*A61B 5/00* (2006.01)
*A61M 16/00* (2006.01)
(Continued)

(52) U.S. Cl.
CPC ............ *A61B 5/743* (2013.01); *A61B 5/0004* (2013.01); *A61B 5/0205* (2013.01); *A61B 5/029* (2013.01);
(Continued)

(58) Field of Classification Search
None
See application file for complete search history.

(56) References Cited

U.S. PATENT DOCUMENTS 4,526,179 A * 7/1985 Salesky .................. 600/589
6,099,481 A 8/2000 Daniels
(Continued)

FOREIGN PATENT DOCUMENTS

JP S61100231 A 5/1986

OTHER PUBLICATIONS

Ingenito, Edward P., et al. "Bronchoscopic lung volume reduction using tissue engineering principles.", 2003, American journal of respiratory and critical care medicine, vol. 167, pp. 771-778.*
(Continued)

*Primary Examiner* — Jacqueline Cheng
*Assistant Examiner* — Jairo Portillo (57) ABSTRACT

Ventilation information may be presented. Output signals may be received that convey information related to one or more breathing parameters of a subject receiving assisted or controlled mechanical ventilation. Based at least in part on the received output signals, volumetric components of a tidal volume of the subject may be determined. The volumetric components may include an alveolar dead space, an effective alveolar tidal volume, and/or other volumetric components. The alveolar dead space is the volume of inspired gas that occupies alveoli but does not take part in oxygen exchange in the lungs of the subject. The effective alveolar tidal volume is the volume of inspired gas that takes part in oxygen exchange in the lungs of the subject. A visual representation that textually or graphically represents the tidal volume, and/or textually or graphically represents the volumetric components separately from each other may be presented via a user interface.

24 Claims, 5 Drawing Sheets

(51) Int. Cl.

| | | |
|---|---|---|
| *G06F 19/00* | (2011.01) | |
| *A61B 5/0205* | (2006.01) | |
| *A61B 5/029* | (2006.01) | |
| *A61B 5/145* | (2006.01) | |
| *A61M 16/04* | (2006.01) | |
| *A61M 16/06* | (2006.01) | |
| *A61M 16/08* | (2006.01) | |

(52) U.S. Cl.
CPC ........ *A61B 5/14542* (2013.01); *A61B 5/4836* (2013.01); *A61B 5/7225* (2013.01); *A61B 5/746* (2013.01); *A61B 5/7475* (2013.01); *A61M 16/00* (2013.01); *A61M 16/0057* (2013.01); *A61M 16/0465* (2013.01); *A61M 16/0666* (2013.01); *A61M 16/085* (2014.02); *A61M 16/0858* (2014.02); *A61M 16/0875* (2013.01); *G06F 19/3406* (2013.01); *A61M 2016/0027* (2013.01); *A61M 2016/0036* (2013.01); *A61M 2205/18* (2013.01); *A61M 2205/505* (2013.01); *A61M 2205/52* (2013.01); *A61M 2230/432* (2013.01); *G06F 19/3487* (2013.01)

(56) References Cited

U.S. PATENT DOCUMENTS

| | | | |
|---|---|---|---|
| 6,306,098 B1* | 10/2001 | Orr | A61B 5/029 128/200.26 |
| 6,342,040 B1 | 1/2002 | Starr et al. | |
| 7,530,353 B2 | 5/2009 | Choncholas et al. | |
| 8,418,693 B2 | 4/2013 | Kaestle et al. | |
| 2003/0227472 A1* | 12/2003 | Westinskow | A61B 5/00 715/700 |
| 2006/0004297 A1* | 1/2006 | Orr | A61B 5/029 600/538 |
| 2007/0068528 A1 | 3/2007 | Bohm | |
| 2007/0144518 A1* | 6/2007 | Acker | A61B 5/0836 128/204.21 |
| 2007/0199566 A1* | 8/2007 | Be'eri | 128/204.23 |
| 2008/0041381 A1* | 2/2008 | Tham | A61M 16/0051 128/204.23 |
| 2008/0281219 A1* | 11/2008 | Glickman | A61B 7/003 600/533 |
| 2009/0024008 A1 | 1/2009 | Brunner et al. | |
| 2010/0101577 A1* | 4/2010 | Kaestle et al. | 128/204.22 |
| 2013/0150734 A1 | 6/2013 | Orr et al. | |

OTHER PUBLICATIONS

Severinghaus et al, "Alveolar dead space as an index of distribution of blood flow in pulmonary capillaries.", 1957, Journal of applied physiology 10.3, p. 335-348.*

Tusman, Gerardo et al "Monitoring Dead Space during Recruitment and PEEP Titration in an Experimental Model", Intensive Care Medicine, vol. 32, No. 11, Sep. 2006, pp. 1863-1871.

Jaffe, Michael B. "Volumetric Capnography, The Next Advance in CO2 Monitoring", Novametrix Medical Systems Inc., Technical Report 2002-1 Rev. 04, Dec. 2, 2002, pp. 1-21.

* cited by examiner

INTUITIVE PRESENTATION OF VENTILATION EFFECTIVENESS

BACKGROUND OF THE INVENTION

1. Field of the Invention

The invention relates to intuitive presentation of ventilation effectiveness including textual and/or graphical representation of respiratory rate, tidal volume, and/or volumetric components of tidal volume.

2. Description of the Related Art

During mechanical ventilation of a subject, various settings such as tidal volume, respiratory rate, and/or other settings may be adjusted on a mechanical ventilator to deliver minute ventilation sufficient to support metabolism. The delivered minute ventilation may be reduced by the presence of dead space, which includes airways and alveoli that are ventilated but do not participate in gas exchange in the lungs of the subject. Ventilation exceeding volume of dead space is thus available for gas exchange, and may be referred to as effective alveolar minute ventilation. The effective alveolar minute ventilation is critical for gas exchange during tidal ventilation. If, for example, a user of a mechanical ventilator (e.g., a caregiver, a therapy decision-maker, etc.) sets the delivered minute ventilation without accounting for loss of ventilation to the dead space, the subject may be under-ventilated.

SUMMARY OF THE INVENTION

One aspect of the invention relates to a method for presenting ventilation information. The method may include receiving output signals conveying information related to one or more breathing parameters of a subject being mechanically ventilated. The method may include determining, based on the received output signals, volumetric components of a tidal volume of the subject. The volumetric components include an alveolar dead space and an effective alveolar tidal volume. The alveolar dead space is the volume of inspired gas that occupies alveoli but does not take part in oxygen exchange in the lungs of the subject. The effective alveolar tidal volume is the volume of inspired gas that takes part in oxygen exchange in the lungs of the subject. The method may include presenting, via a user interface, a visual representation that textually or graphically represents the tidal volume and the volumetric components.

Another aspect of the invention relates to a system for presenting ventilation information. The system may include one or more processors configured to execute computer program modules. The computer program modules may include a communications module configured to receive output signals conveying information related to one or more breathing parameters of a subject being mechanically ventilated. The computer program modules may include a tidal parameter determination module configured to determine, based on the received output signals, volumetric components of a tidal volume of the subject. The volumetric components may include an alveolar dead space and an effective alveolar tidal volume. The alveolar dead space is the volume of inspired gas that occupies alveoli but does not take part in oxygen exchange in the lungs of the subject. The effective alveolar tidal volume is the volume of inspired gas that takes part in oxygen exchange in the lungs of the subject. The computer program modules may include a data presentation module configured to facilitate presenting, via a user interface, a visual representation that textually or graphically represents the tidal volume and the volumetric components.

Yet another aspect of the invention relates to a system for presenting ventilation information. The system may include communications means for receiving output signals conveying information related to one or more breathing parameters of a subject being mechanically ventilated. The system may include tidal parameter determination means for determining, based on the received output signals, volumetric components of a tidal volume of the subject. The volumetric components may include an alveolar dead space and an effective alveolar tidal volume. The alveolar dead space is the volume of inspired gas that occupies alveoli but does not take part in oxygen exchange in the lungs of the subject. The effective alveolar tidal volume is the volume of inspired gas that takes part in oxygen exchange in the lungs of the subject. The system may include data presentation means for presenting a visual representation that textually or graphically represents the tidal volume and the volumetric components.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein are drawn to scale. It is to be expressly understood, however, that the drawings are for the purpose of illustration and description only and are not a limitation of the invention. In addition, it should be appreciated that structural features shown or described in any one embodiment herein can be used in other embodiments as well. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
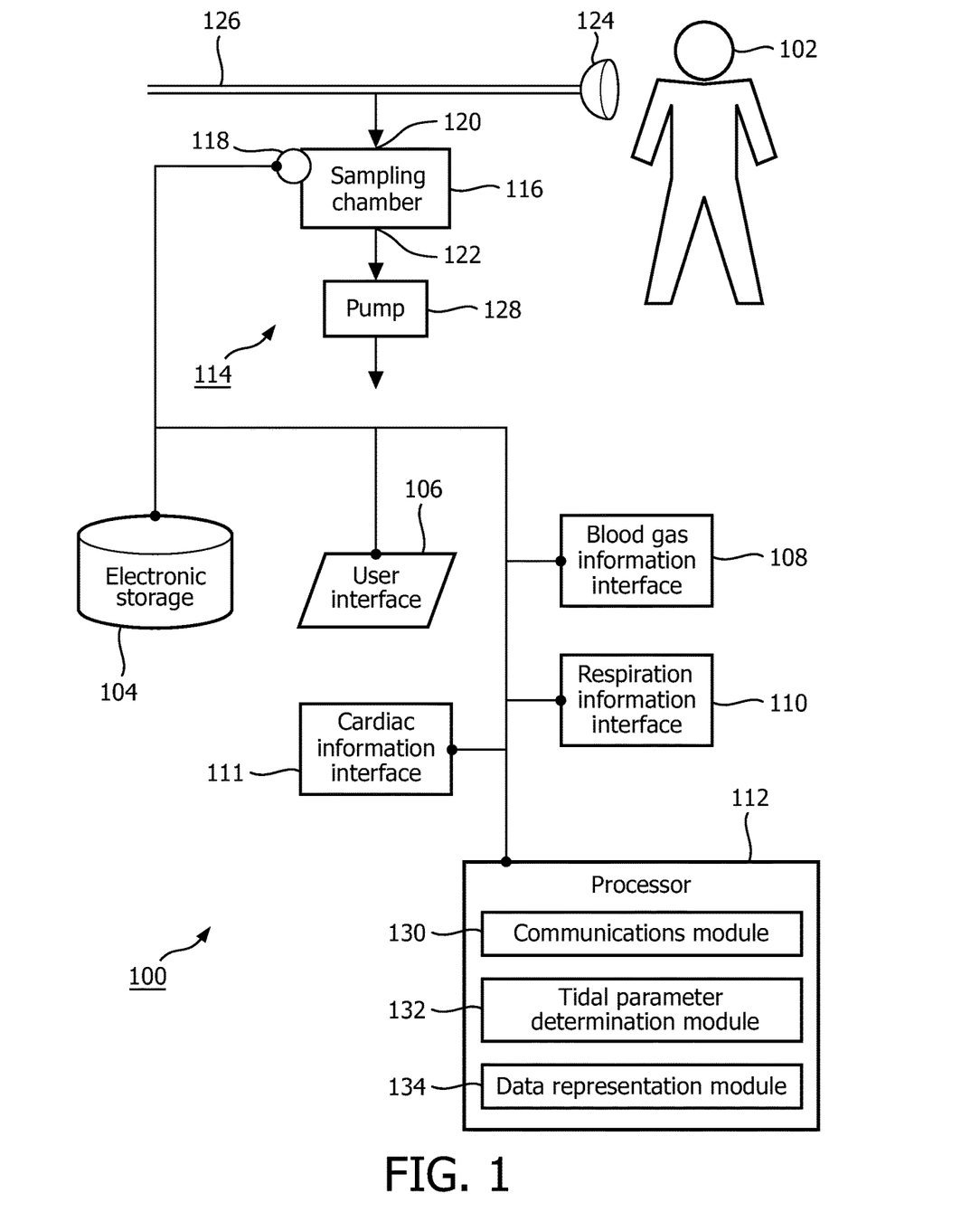
FIG. 1 illustrates an exemplary system configured to monitor respiratory rate, tidal volume, and/or volumetric components of tidal volume.

FIG. 1 illustrates a system 100 configured to monitor respiratory rate, tidal volume, and volumetric components of tidal volume, according to exemplary embodiments of the present invention. Such monitoring may be performed during mechanical ventilation of a subject 102. In order to, among other advantages, aid a user of a mechanical ventilator and/or the system 100 (e.g., the user, a caregiver, a therapy decision-maker, etc.) to apply proper settings to the mechanical ventilator such that the subject 102 is adequately ventilated, the system 100 presents ventilation information to the user in an intuitive manner.

Tidal volume delivered to the subject 102 can be divided into different volumetric components according to the gas exchange efficiency of the lungs, or part of the lung, of the subject 102 being ventilated. Examples of these volumetric components include airway dead space, alveolar dead space, alveolar tidal volume, effective alveolar tidal volume and/or other volumetric components. The airway dead space is the volume of the airway between the external orifices of the subject 102 and the alveoli within the lungs of the subject 102, and may further include apparatus dead space of a mechanical ventilator. The alveolar dead space is the volume within the lungs at which the alveoli do not function adequately in conjunction with the pulmonary blood to exchange gas in the blood. The alveolar tidal volume is the tidal volume less the airway dead space, and the effective alveolar tidal volume is the tidal volume less the airway dead space and the alveolar dead space. The airway dead space remains substantially unchanged during respiration, whereas the alveolar dead space may change over time, but these changes are not especially dynamic unless lung injury status has changed drastically or ventilation/perfusion matching has been substantially altered.

The volumetric components of the tidal volume may be provided by volumetric capnography, arterial blood gas measurements, and/or other measurement or calculation techniques. The volumetric components of the tidal volume may be updated on a breath-by-breath basis, for example, as related information from a mainstream volumetric capnometer is made available. The tidal volume components can be presented in a breath-by-breath manner in textual and/or graphical form, which makes analysis of such information as well as the relationship among the volumetric components more intuitive for the user. According to some embodiments, breath movement is animated by a graphical element, which reflects the relative size of subsequent breaths, a reference normal value, and/or other information relating to the ventilation of the subject 102. The textual and/or graphical presentation of ventilation information on a breath-by-breath basis may support integrated clinical decisions and provide timely updates when the user acts upon the information.

In some embodiments, the system 100 includes an electronic storage 104, a user interface 106, a blood gas information interface 108, a respiration information interface 110, a processor 112, and/or other components. In one embodiment, the system 100 includes one or more components that provide therapy to the subject 102. For example, the system 100 may include a ventilator (not depicted) configured to facilitate respiration by the subject 102. One or more of the settings of the ventilator may be adjusted automatically by the processor 112 based on the ongoing determination of various ventilation information.

The electronic storage 104 comprises electronic storage media that electronically stores information. The electronic storage media of the electronic storage 104 may include one or both of system storage that is provided integrally (i.e., substantially non-removable) with the system 100 and/or removable storage that is removably connectable to the system 100 via, for example, a port (e.g., a USB port, a firewire port, etc.) or a drive (e.g., a disk drive, etc.). The electronic storage 104 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. The electronic storage 104 may store software algorithms, information determined by the processor 112, information received via the user interface 106, and/or other information that enables the system 100 to function as described herein. The electronic storage 104 may be a separate component within the system 100, or the electronic storage 104 may be provided integrally with one or more other components of the system 100 (e.g., the processor 112).

The user interface 106 is configured to provide an interface between system 100 and the user through which the user may provide information to and receive information from the system 100. This enables data, results, and/or instructions and any other communicable items, collectively referred to as "information," to be communicated between the user and the system 100. Examples of interface devices suitable for inclusion in the user interface 106 include one or more of a keypad, buttons, switches, a keyboard, knobs, levers, a display screen, a touch screen, speakers, a microphone, an indicator light, an audible alarm, a printer, and/or other interface devices.

It is to be understood that other communication techniques, either hard-wired or wireless, are also contemplated by the present invention as the user interface 106. For example, the present invention contemplates that the user interface 106 may be integrated with a removable storage interface provided by the electronic storage 104. In this example, information may be loaded into the system 100 from removable storage (e.g., a smart card, a flash drive, a removable disk, etc.) that enables the user to customize implementations of the system 100. Other exemplary input devices and techniques adapted for use with the system 100 as the user interface 106 include, but are not limited to, an RS-232 port, RF link, an IR link, modem (telephone, cable, or other). In short, any technique for communicating information with the system 100 is contemplated by the present invention as the user interface 106.

The blood gas information interface 108 is configured to receive blood gas information. Blood gas information includes information related to one or more blood gas parameters. The blood gas parameters indicate concentrations (e.g., partial pressure) of one or more molecular species in the blood of the subject 102. By way of non-limiting example, the one or more molecular species may include one or more of oxygen, carbon dioxide, bicarbonate, and/or other molecular species. In one embodiment, the blood gas information interface 108 includes an electronic port, lead, wireless receiver, and/or other components enabling electronic reception of blood gas information to the system 100. The blood gas information may be received electronically from a detector configured to measure the one or more blood gas parameters. In one embodiment, the blood gas information interface 108 includes a user interface (e.g., the user interface 106) through which the user can manually input the blood gas information. In one embodiment, blood gas information is entered manually from a printout, a patient chart, a log book, and/or some other reference. The blood gas information interface 108 may be configured to provide output signals conveying blood gas information and/or other information to one or more other components of the system 100 (e.g., the processor 112). In some embodiments, the cardiac information interface 111 includes and electronic port, lead, wireless receiver, and/or other component enabling electronic reception of cardiac information from one or more sensors.

The respiration information interface 110 is configured to receive respiration information. Respiration information includes information related to one or more respiration parameters of the breathing of the subject 102. The one or more respiration parameters may include one or more of pressure, flow rate, tidal volume, alveolar tidal volume, composition (e.g., partial pressure(s), concentration(s), etc.), expired carbon dioxide, expired oxygen, respiratory rate, volume of expired carbon dioxide, mixed expired carbon dioxide fraction, airway dead volume, apparatus dead volume, and/or other respiration parameters. The respiration information interface 110 may be configured to provide output signals conveying respiration information and/or other information to one or more other components of the system 100 (e.g., the processor 112). In one embodiment, the respiration information interface 110 includes an electronic port, lead, wireless receiver, and/or other component enabling electronic reception of respiration information from one or more sensors and/or a respiration detector 114.

The cardiac information interface 111 is configured to receive cardiac information. Cardiac information include information related to one or more cardiac parameters of the subject 102. The one or more cardiac parameters may include one or more of cardiac output, pulmonary capillary blood flow, heart rate, saturation of peripheral oxygen ($S_pO_2$), and/or other cardiac parameters. The cardiac information interface 111 may be configured to provide output signals conveying cardiac information and/or other information to one or more other components of the system 100 (e.g., the processor 112). In some embodiments, the cardiac information interface 111 includes and electronic port, lead, wireless receiver, and/or other component enabling electronic reception of cardiac information from one or more sensors.

The respiration detector 114 is configured to obtain gas from at or near the airway of the subject 102. According to some embodiments, the respiration detector 114 may generate output signals conveying information obtained from measurements taken from the obtained gas, which may be provided to other components of the system 100 (e.g., the processor 112). In one embodiment, the respiration detector 114 includes a sampling chamber 116 and a sensor 118.

The sampling chamber 116 is configured to receive gas obtained at or near the airway of the subject 102. The gas flows through the sampling chamber 116 from an inlet 120 to an outlet 122. The gas is conveyed to the sampling chamber 116 via a subject interface appliance 124 and/or a conduit 126. The subject interface appliance 124 may engage one or more orifices of the airway of the subject 102 in a sealed or unsealed manner. Some examples of the subject interface appliance 124 may include, for example, an endotracheal tube, a nasal cannula, a tracheotomy tube, a nasal mask, a nasal/oral mask, a full face mask, a total face mask, a partial rebreathing mask, and/or other interface appliances that communicate a flow of gas with an airway of a subject. The present invention is not limited to these examples, and contemplates implementation of any subject interface. The sampling chamber may be placed directly in conduit 126. In this configuration, a pump 128 may not be needed.

The conduit 126 is configured to place the inlet 120 of the sampling chamber 116 in fluid communication with the subject interface appliance 124 such that gas obtained by the subject interface appliance 124 from at or near the airway of the subject 102 is provided to the inlet 120 via the conduit 126. In one embodiment, the respiration detector 114 is configured for side-stream sampling. In this configuration, the conduit 126 is further configured to place the subject interface appliance 124 in fluid communication with a source of a breathable substance. For example, a flow of breathable gas may be delivered to the subject 102 through the conduit 126 having one or more parameters that are controlled in accordance with a therapy regime. The one or more parameters of the flow of breathable gas that are controlled may include one or more of pressure, flow rate, composition, humidity, temperature, and/or other parameters. In one embodiment, the respiration detector 114 is configured for mainstream sampling. In this configuration, the sampling chamber 116 is disposed within the flow path through the conduit 126, rather than being disposed off to the side (as is shown in FIG. 1). In one embodiment in which the respiration detector 114 is configured for side-stream sampling, or in which the conduit 126 does not provide for provision of a breathable substance to the airway of the subject 102, the pump 128 is configured to draw gas from the conduit 126 into the sampling chamber 116 through the inlet 120.

The sensor 118 is configured to generate output signals conveying information related to one or more parameters of the gas within the sampling chamber 116. By way of non-limiting example, the one or more parameters of the gas may include composition, pressure, flow rate, and/or other parameters. In one embodiment, since the gas within the sampling chamber 116 has been obtained from at or near the airway of the subject 102, the output signals generated by the sensor 118 become the respiration information communicated to the system 100 through the respiration information interface 110. In one embodiment, the sampling chamber 116 includes one or more components that process (at least preliminarily) the output signals of sensor 118 before communicating the respiration information to the system 100 through the respiration information interface 110.

It will be appreciated that the illustration of the sensor 118 in FIG. 1 as a single component is not intended to be limiting. In one embodiment, the sensor 118 includes a plurality of sensors. Further, the location of the sensor 118 within the sampling chamber 116 is not intended to be limiting. The sensor 118 may include one or more sensing units disposed in the conduit 126, the subject interface appliance 124, at the source of the breathable substance, at or near the pump 128, and/or disposed at other locations outside of the sampling chamber 116. For example, the sensor 118 may include a sensor disposed in the conduit 126 to measure airway dead volume, tidal volume, volume of expired carbon dioxide, and/or other parameters.

The processor 112 is configured to provide information processing capabilities in the system 100. As such, the processor 112 may include one or more of a digital processor, an analog processor, a digital circuit designed to process information, an analog circuit designed to process information, a state machine, and/or other mechanisms for electronically processing information. Although the processor 112 is shown in FIG. 1 as a single entity, this is for illustrative purposes only. In some implementations, the processor 112 may include a plurality of processing units. These processing units may be physically located within the same device, or the processor 112 may represent processing functionality of a plurality of devices operating in coordination.

As is shown in FIG. 1, the processor 112 is configured to execute one or more computer program modules. The one or more computer program modules may include one or more of a communications module 130, a tidal parameter determination module 132, a data presentation module 134, and/or other modules. The processor 112 may be configured to execute the modules 130, 132, and/or 134 by software; hardware; firmware; some combination of software, hardware, and/or firmware; and/or other mechanisms for configuring processing capabilities on processor 112.

It should be appreciated that although the modules 130, 132, and 134 are illustrated in FIG. 1 as being co-located within a single processing unit, in implementations in which the processor 112 includes multiple processing units, one or more of the modules 130, 132, and/or 134 may be located remotely from the other modules. The description of the functionality provided by the modules 130, 132, and/or 134 described below is for illustrative purposes, and is not intended to be limiting, as any of the modules 130, 132, and/or 134 may provide more or less functionality than is described. For example, one or more of the modules 130, 132, and/or 134 may be eliminated, and some or all of its functionality may be provided by other ones of the modules 130, 132, and/or 134. As another example, the processor 112 may be configured to execute one or more additional modules that may perform some or all of the functionality attributed below to one of the modules 130, 132, and/or 134.

The communications module 130 may be configured to receive output signals conveying information related to one or more cardiac parameters, one or more breathing parameters, and/or other parameters associated with the subject 102. Such output signals may be received from the blood gas information interface 108, the respiration information interface 110, the cardiac information interface 111, the respiration detector 114, the sensor 118, other components of the system 100, and/or other sources. The communications module 130 may be configured to transfer information between the user interface 106 and the processor 112.

The tidal parameter determination module 132 may be configured to determine, based on the output signals received by the communications module 130, volumetric components of a tidal volume of the subject 102. The volumetric components may include one or more of an airway dead space, an alveolar dead space, an alveolar tidal volume, an effective alveolar tidal volume, and/or other volumetric components. As discussed above, the airway dead space is the volume of the airway between the external orifices of the subject 102 and the alveoli within the lungs of the subject 102, and may further include apparatus dead space of a mechanical ventilator. The alveolar dead space is the volume of inspired gas that occupies alveoli but does not take part in oxygen exchange in the lungs of the subject 102. In some embodiments, the alveolar dead space may be determined as a fraction or percentage (e.g., 5% or 15%) of the alveolar tidal volume. The alveolar tidal volume is the tidal volume less the airway dead space. The effective alveolar tidal volume is the volumetric portion of alveolar tidal volume that has matching blood perfusion and thus takes part in gas exchange in the lungs of the subject 102.

A determination of dead space fraction of the subject 102 may be performed by the tidal parameter determination module 132 in order to determine one or more volumetric components. In one embodiment, the tidal parameter determination module 132 is configured to determine dead space fraction of the subject 102 according to the following relationship:

$$Vd/Vt = \frac{(PaCO_2 - PeCO_2)}{PaCO_2}; \qquad (1)$$

where Vd/Vt represents dead space fraction with $V_d$ representing the total or physiologic dead space (i.e., sum of airway dead space, alveolar dead space, and/or other dead space) and $V_t$ representing the tidal volume, $PaCO_2$ represents the partial pressure of carbon dioxide in arterial blood, and $PeCO_2$ represents the mixed expired carbon dioxide for a given breath (e.g., may be an average, a mean, and/or some other aggregated measurement, or may be measured for a single breath). As will be appreciated, $PaCO_2$ is a blood gas parameter and $PeCO_2$ is a respiration parameter. As such, in a given determination of dead space fraction, the value used for $PaCO_2$ may be "old" (e.g., the same as for a previous determination of volumetric components), while the value used for $PeCO_2$ is "new" (e.g., obtained since the previous determination of volumetric components). From dead space fraction and tidal volume, the total or physiologic dead space may be derived according to the following relationship:

$$Vd = Vt \cdot Vd/Vt \qquad (2)$$

In some embodiments, the airway dead space may be obtained from a volumetric capnography curve by means of the Fowler's dead space method, which is known to those skilled in the art. Other methods for determining the airway dead space are contemplated and are within the scope of the present invention. As mentioned, the alveolar tidal volume is the tidal volume less the airway dead space. The airway dead space (and the apparatus dead space, if applicable) is subtracted from the total or physiologic dead space to yield the alveolar dead space. The alveolar tidal volume less the alveolar dead space equals the effective alveolar tidal volume.

It will be appreciated that the particular relationships used to determine volumetric components described above is not intended to be limiting. The scope of this disclosure includes at least any other relationships that enable updated determinations of volumetric components to be made based on new respiration information, blood gas information, and/or other information that has been used in one or more current or previous determinations of volumetric components.

The data presentation module 134 may be configured to present ventilation information. Such ventilation information may include respiratory rate, tidal volume, volumetric components of tidal volume, and/or other information related to ventilation of the subject 102. The data presentation module 134 may be configured to present the ventilation information via the user interface 106. This may provide updated ventilation information to the user in a substantially ongoing manner. This may enhance diagnosis and/or treatment of subject 102 by the user. The presented ventilation information may include one or more visual representations of the ventilation information. For example, a visual representation may textually or graphically represent the tidal volume. A visual representation may textually or graphically represent the volumetric components separately from each other. In some embodiments, the data presentation module 134 may be configured to provide an indicator representing a reference tidal volume, reference values of volumetric components, and/or other reference parameters, which may be based on one or more previous breaths and/or published physiological data.

According to some embodiments, a visual representation presented by the data presentation module 134 may include a math column that textually represents the tidal volume and the volumetric components. As such, the tidal volume and the volumetric components may be arranged in the math column with arithmetic operators to convey an arithmetic relationship between the tidal volume and the volumetric components. An exemplary math column is described in connection with FIG. 2.

A visual representation presented by the data presentation module 134, in some embodiments, may include a stacked bar plot that graphically represents the tidal volume and the volumetric components. The stacked bar plot may include one or more bars, where individual ones of the one or more bars represent the tidal volume at different time intervals. Individual ones of the one or more bars may include at least two bar segments stacked from a base line. The at least two bar segments may include a first bar segment stacked farthest from the baseline. The first bar segment may represent the effective alveolar tidal volume. An exemplary stacked bar plot is described in connection with FIG. 3.

According to some embodiments, a visual representation presented by the data presentation module 134 may include a time based series of images. Regions within the images may be proportional to tidal volume, one or more volumetric components, and/or other parameters. The series of images may be view individually, as an array, as an animated sequence, and/or other format.

In some embodiments, a visual representation presented by the data presentation module 134 may include a graphical element pictorially representing at least a portion of a human respiratory system. A dimension of the graphical element as a whole may correspond to the tidal volume. Such a graphical element may include at least two regions. The at least two regions may include a first region having a dimension corresponding to the alveolar dead space, and a second region having a dimension corresponding to the effective alveolar tidal volume. The graphical element may be animated such that the respective dimensions of the graphical element and the at least two regions change during respiration of the subject to reflect the flow of gas into and out of the at least two regions during respiration. An exemplary graphical element pictorially representing at least a portion of a human respiratory system is described in connection with FIG. 4.

In accordance with some embodiments, a visual representation presented by the data presentation module 134 may include a graphical element pictorially representing one or more alveolus shapes. A dimension of the graphical element may correspond to the tidal volume. The graphical element may include at least two regions. The at least two regions may include a first region having a dimension corresponding to the alveolar dead space, and a second region having a dimension corresponding to the effective alveolar tidal volume. The graphical element may be animated such that the respective dimensions of the graphical element and the at least two regions change during respiration of the subject to reflect the flow of gas into and out of the at least two regions during respiration. An exemplary graphical element pictorially representing one or more alveolus shapes is described in connection with FIG. 5.

The data presentation module 134 may be configured to present multiple visual representations of the same ventilation information. For example, the data presentation module 134 may present multiple ones of a math column, a stacked bar plot, a graphical element pictorially representing at least a portion of a human respiratory system, a graphical element pictorially representing an alveolus shape, and/or other visual representations. The multiple visual representations and/or portions thereof may be coordinated in appearance, such as for example, by color, texture, and/or other visual distinctions. This may allow the user to easily identify volumetric components conveyed by different visual representations, to relate ventilation information to individual breaths of the subject 102, to relate ventilation information to a trend of breaths over time, and/or to use the ventilation information for other purposes.

The data presentation module 134 may be configured to present information associated with the subject 102 other than ventilation information. For example, the status module 134 may textually or graphically present blood perfusion information as it relates to effective gas exchange. Such information may include one or more of magnitude of cardiac output, magnitude of shunt, oxygen saturation of blood, heart rate, and/or other information.

Figure 2:
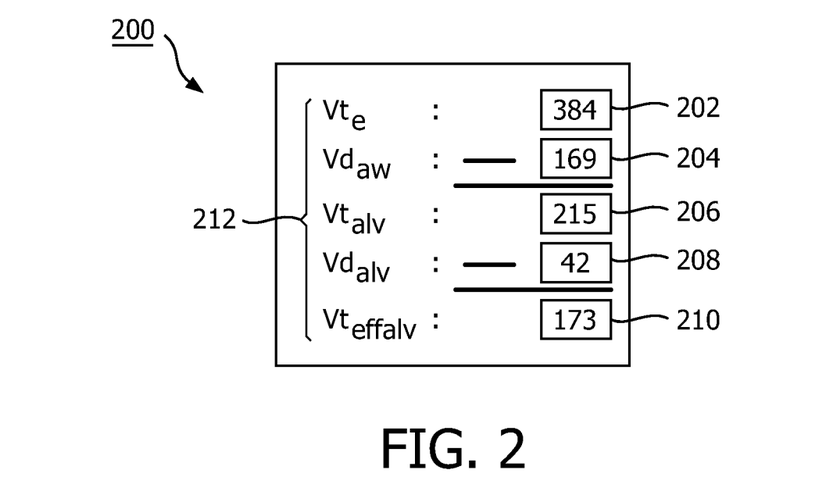
FIG. 2 illustrates an exemplary math column textually representing tidal volume and volumetric components thereof.

FIG. 2 illustrates an exemplary math column 200 textually representing tidal volume and volumetric components thereof. The math column 200 may be presented to the user via the user interface 106. As depicted in FIG. 2, the math column 200 includes field 202, field 204, field 206, field 208, and field 210, along with corresponding field labels 212. One or more of the fields 202-210 may be omitted from the math column 200 or combined with other ones of the fields 202-210. Additional fields with or without corresponding field labels may be included in the math column 200. In some embodiments, the field labels 212 may be omitted, or may include other visual indications (e.g., icons, other graphic labels, and/or other text labels) relating to corresponding fields. The fields 202-210 and/or the field labels 212 may be coordinated in appearance, such as for example, by color, texture, and/or other visual distinctions. Such appearance coordination may be consistent with one or more other visual representations presented by the user interface 106.

According to the embodiment depicted in FIG. 2, the field 202 presents tidal volume of the subject 102 ("384" is a sample value) and is labeled as $Vt_e$. The field 204 presents airway dead space of the subject 102 ("169" is a sample value) and is labeled as $Vd_{aw}$. The field 206 presents alveolar tidal volume of the subject 102 ("215" is a sample value) and is labeled as $Vt_{alv}$. The field 208 presents alveolar dead space of the subject 102 ("42" is a sample value) and is labeled as $Vd_{alv}$. The field 210 presents effective alveolar tidal volume of the subject 102 ("173" is a sample value) and is labeled as $Vt_{effalv}$.

An arithmetic relationship between the tidal volume and/or the volumetric components may be quantitatively conveyed by the math column 200. In FIG. 2, the arithmetic relationship is that the tidal volume equals the sum of the volumetric components. Arithmetic operators such as a plus sign (e.g., "+"), a minus sign (e.g., "−"), a multiply sign (e.g., "×"), a divide sign (e.g., "÷"), and/or other operators may be used to convey an arithmetic relationship. In the math column 200, a value in the field 204 is subtracted from a value in the field 202 to yield a value in the field 206. This operation is indicated by a minus sign beside the field 204. Similarly, a value in the field 208 is subtracted from a value in the field 206 to yield a value in the field 210. This operation is indicated by a minus sign beside the field 208.

From the arrangement of the fields 202-210, the user may intuitively determine, for example, that tidal volume delivered to the subject 102 should be larger that the sum of the airway dead space and the alveolar dead space in order for the subject 102 to receive any effective alveolar tidal volume. The arrangement of the fields 202-210 depicted in FIG. 2 is not intended to be limiting as other arrangements are contemplated. For example, elements of the math column 200 may be arranged so as to show the same arithmetic relationship in another form, or a different relationship between one or more of the tidal volume, one or more of the volumetric components, and/or other information.

Figure 3:
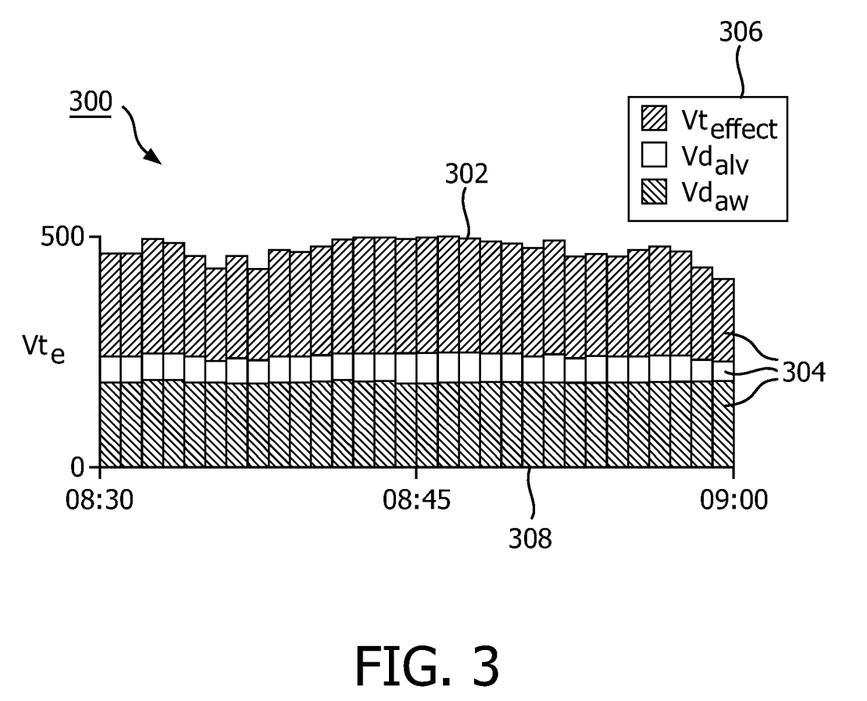
FIG. 3 illustrates an exemplary stacked bar plot graphically representing tidal volume and volumetric components thereof.

FIG. 3 illustrates an exemplary stacked bar plot 300 graphically representing tidal volume and volumetric components thereof. The stacked bar plot 300 may be presented to the user via the user interface 106. As depicted in FIG. 3, the stacked bar plot 300 includes a number of bars such as bar 302. Individual ones of the bars included in the stacked bar plot 300 represent ventilation information at different time intervals. Individual ones of the bars included in the stacked bar plot 300 include three bar segments such as bar segments 304. In some embodiments, individual ones of the bars included in the stacked bar plot 300 include two or more bar segments. The bar segments may be coordinated in appearance, such as for example, by color, texture, and/or other visual distinctions. Such appearance coordination may be consistent with one or more other visual representations presented by the user interface 106. The stacked bar plot 300 may include a legend 306 to convey what particular information corresponds to various bars and/or bar segments.

According to the embodiment depicted in FIG. 3, bar segments for a given bar are arranged such that a bar segment stacked closest to baseline 308 represents the airway dead space, a bar segment stacked above that bar segments represents the alveolar dead space, and a bar segments stacked furthest from the baseline 308 represents the effective alveolar tidal volume. The total height of a given bar may represent tidal volume. As such, an arithmetic relationship between the tidal volume and/or the volumetric components may be conveyed by the stacked bar plot 300 since the tidal volume equals the sum of the volumetric components. Some embodiments may assign a constant value to one or more bar segments (e.g., a bar segment representing airway dead space). In some embodiments, airway dead space may not be presented and, as such, the total height of a given bar may represent alveolar tidal volume.

Figure 4:
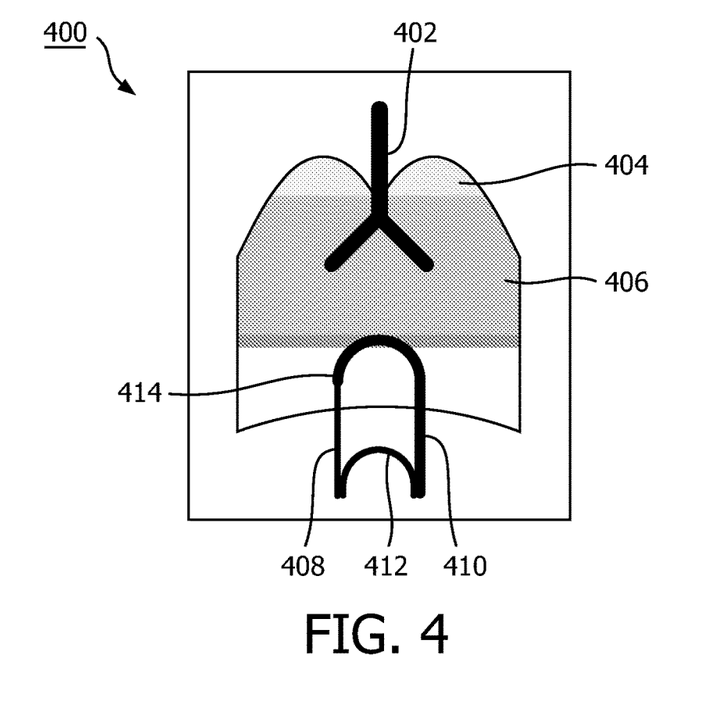
FIG. 4 illustrates an exemplary graphical element pictorially representing at least a portion of a human respiratory system and conveying information relating to respiratory rate, tidal volume, and/or volumetric components of tidal volume.

FIG. 4 illustrates an exemplary graphical element 400 pictorially representing at least a portion of a human respiratory system and conveying information relating to respiratory rate, tidal volume, and/or volumetric components of tidal volume. In FIG. 4, the at least a portion of a human respiratory system includes lungs represented by a lungs shape. In the embodiment depicted in FIG. 4, the graphical element 400 pictorially represents a lung such as that of the subject 102. The overall size or other dimension of the graphical element 400 represents tidal volume. The graphical element 400 includes region 402, region 404, region 406, and/or other regions. One or more of the regions 402-406 may be omitted from the graphical element 400, combined with other ones of the regions 402-406, or positioned differently in the graphical element 400. The regions 402-406, other regions, and/or other visible aspects of the graphical element 400 may be coordinated in appearance, such as for example, by color, texture, and/or other visual distinctions. Such appearance coordination may be consistent with one or more other visual representations presented by the user interface 106.

According to the embodiment depicted in FIG. 4, the region 402 represents airway dead space, the region 404 represents alveolar dead space, and the region 406 represents effective alveolar tidal volume. The relative size, area, or other dimension of the regions 402-406 may correspond qualitatively or quantitatively to values for volumetric components associated with the regions 402-406. The graphical element 400 may be animated such that certain characteristics (e.g., size, color, etc.) of the regions 402-406 and/or the graphical element 400 itself change during respiration of the subject 102. For example, the area of the regions 402-406 may increase and/or be filled by color during respiration of the subject 102 to reflect the flow of gas into and out of the regions 402-406 during respiration. Animation of the graphical element 400 may be performed on a breath-by-breath basis. As such, expansion and contraction of the graphical element 400 and/or the regions 402-406 may be tied to the breathing rate of the subject 102. A reference normal value for one or more of the regions 402-406 may be included in the graphical element 400. In some embodiments, an ideal tidal volume for a given weight of the subject 102 may be represented by one or more regions (not depicted). The graphical element 400 may include one or more regions representing volumetric difference between two consecutive breaths, volumetric difference between monitored breaths and reference data, and/or other information. An exemplary animation of a graphical element is described below in connection with FIG. 6.

The graphical element 400 may include perfusion region 408, perfusion region 410, perfusion region 412, and/or other perfusion regions. The perfusion regions 408-412 represent blood flow through the lungs of the subject 102. More specifically, the perfusion region 408 represents deoxygenated blood returning to the lungs from other parts of the subject 102. The perfusion region 410 represents blood that is oxygenated through gas exchange in the lungs as it flows through the perfused region of the lungs that is matched to ventilated alveoli. The perfusion region 412 represents blood that bypasses the ventilated portion of the lungs and thus is not oxygenated. The perfusion region 412 may be positioned within or outside the lungs shape in various embodiments. Information conveyed by the perfusion regions 408-412 may be obtained from the blood gas information interface 108, the cardiac information interface 111, and/or other sources.

The position of a point 414 where the perfusion region 408 meets the perfusion region 410 may be indicative of how effective the lungs of the subject 102 are at providing oxygen to the bloodstream. In one embodiment, for example, if the lungs are good at oxygenating blood, then the position of the point 414 may be similar to the position of the point 414 depicted in FIG. 4. If the lungs are poor at oxygenating blood, then the position of the point 414 may be shifted to the right relative to the position of the point 414 depicted in FIG. 4. Blood flow rate, heart rate, and/or other factors may be represented by a dimension (e.g., width) or animation (e.g., pulsating movement) of one or more of the perfusion regions 408-412.

Figure 5:
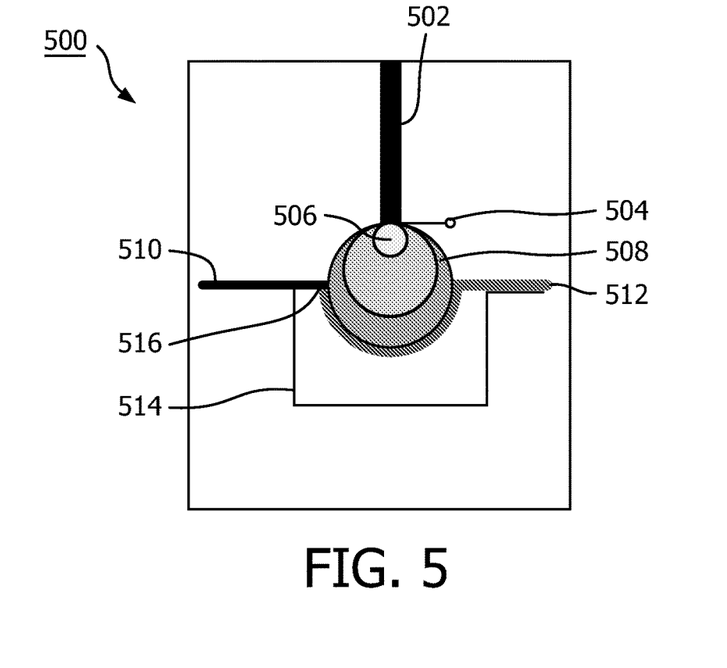
FIG. 5 illustrates an exemplary graphical element pictorially representing one or more alveoli shapes and conveying information relating to respiratory rate, tidal volume and/or volumetric components of tidal volume.

FIG. 5 illustrates an exemplary graphical element 500 pictorially representing one or more alveolus shapes and conveying information relating to respiratory rate, tidal volume, and/or volumetric components of tidal volume. The graphical element 500 includes region 502, region 504, region 506, and/or other regions. One or more of the regions 502-506 may be omitted from the graphical element 500 or combined with other ones of the regions 502-506. The regions 502-506, other regions, and/or other visible aspects of the graphical element 500 may be coordinated in appearance, such as for example, by color, texture, and/or other visual distinctions. Such appearance coordination may be consistent with one or more other visual representations presented by the user interface 106.

According to the embodiment depicted in FIG. 5, the region 502 represents airway dead space, the region 504 represents alveolar dead space, and the region 506 represents effective alveolar tidal volume. The relative size, area, or other dimension of the regions 502-506 may correspond qualitatively or quantitatively to values for volumetric components associated with the regions 502-506. The graphical element 500 may be animated such that certain characteristics (e.g., size, color, etc.) of the regions 502-506 and/or the graphical element 500 itself change during respiration of the subject 102. For example, the area of the regions 502-506 may increase and/or be filled by color during respiration of the subject 102 to reflect the flow of gas into and out of the regions 502-506 during respiration. Animation of the graphical element 500 may be performed on a breath-by-breath basis. As such, expansion and contraction of the graphical element 500 and/or the regions 502-506 may be tied to the breathing rate of the subject 102. A reference circle 508 may indicate, after expiration, how large the effective alveolar tidal volume was for a previous breath by the subject 102. A reference normal value for one or more of the regions 502-506 may be included in the graphical element 500. The graphical element 500 may include one or more regions representing volumetric difference between two consecutive breaths, volumetric difference between monitored breaths and reference data, and/or other information. An exemplary animation of a graphical element is described in connection with FIG. 6.

The graphical element 500 may include perfusion region 510, perfusion region 512, perfusion region 514, and/or other perfusion regions. The perfusion regions 510-514 represent blood flow through the lungs of the subject 102. More specifically, the perfusion region 510 represents deoxygenated blood returning to the lungs from other parts of the subject 102. The perfusion region 512 represents blood that is oxygenated through gas exchange in the lungs as it flows through the perfused region of the lungs that is matched to ventilated alveoli. The perfusion region 514 represents blood that bypasses the ventilated portion of the lungs and thus is not oxygenated. Information conveyed by the perfusion regions 510-514 may be obtained from the blood gas information interface 108, the cardiac information interface 111, and/or other sources.

The position of a point 516 where the perfusion region 510 meets the perfusion region 512 may be indicative of how effective the lungs of the subject 102 are at providing oxygen to the bloodstream. In one embodiment, for example, if the lungs are good at oxygenating blood, then the position of the point 516 may be similar to the position of the point 516 depicted in FIG. 4. If the lungs are poor at oxygenating blood, then the position of the point 516 may be shifted to the right relative to the position of the point 516 depicted in FIG. 4. Blood flow rate, heart rate, and/or other factors may be represented by a dimension (e.g., width) or animation (e.g., pulsating movement) of one or more of the perfusion regions 510-514.

Figure 6:
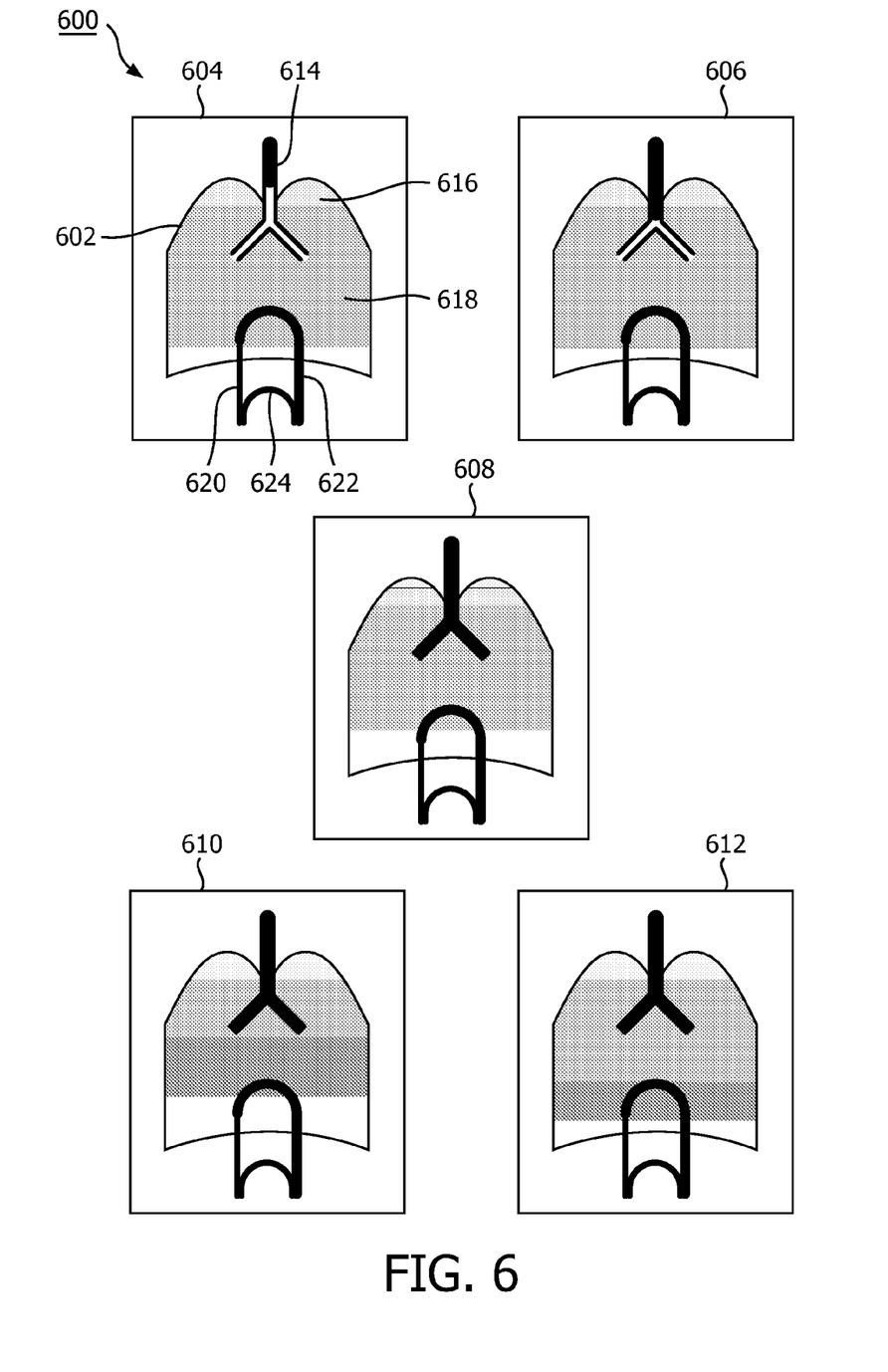
FIG. 6 illustrates frames of an exemplary animation of a graphical element.

FIG. 6 illustrates frames 600 of an exemplary animation of a graphical element 602. As depicted in FIG. 6, the frames 600 pictorially represent at least a portion of a human respiratory system and convey information relating to respiratory rate, tidal volume, and/or volumetric components of tidal volume. Although the graphical element 602 in the frames 600 generally corresponds to the graphical element 400 depicted in FIG. 4, the concepts discussed herein for animating a graphical element are applicable to other visual representations such as those described in connection with FIGS. 2-5 and/or other visual representations of ventilation information. In FIG. 6, the frames 600 include frame 604, frame 606, frame 608, frame 610, and frame 612, however more or less frames may be utilized during animation of the graphical element 602.

The graphical element 602 shown in frames 604-612 includes region 614 representing airway dead space, region 616 representing alveolar dead space, region 618 representing effective alveolar tidal volume, perfusion region 620 representing deoxygenated blood returning to the lungs from other parts of the subject 102, perfusion region 622 representing blood that is oxygenated through gas exchange in the lungs as it flows through the perfused region of the lungs that are matched to ventilated alveoli, perfusion region 624 representing blood that bypasses the ventilated portion of the lungs and thus is not oxygenated. One or more regions of the graphical element 602 (e.g., the regions 614-618, the perfusion regions 620-624, and/or other regions) may be omitted from the graphical element 602 or combined with other ones of the regions. The regions 614-618, the perfusion regions 620-624, and/or other visible aspects of the graphical element 602 may be coordinated in appearance, such as for example, by color, texture, and/or other visual distinctions. Such appearance coordination may be consistent with one or more other visual representations presented by the user interface 106.

The frame 604 represents an early point in the breathing cycle of the subject 102 in which gas begins to fill the airway to the lungs. The region 614 can be seen as partially filled. The frame 606 represents a later point in the breathing cycle of the subject 102. The region 614 is filled further, relative to the frame 604. The overall size of the graphical element 602 is increased and the widths of the perfusion regions 620 and 622 are increased, relative to the frame 604, due to inspiration of respiratory gas and pulsation of blood. The frame 608 represents a yet later point in the breathing cycle of the subject 102. The region 614 is completely filled, and the region 616 is partially filled. The overall size of the graphical element 602 is increased, relative to the frame 606. The frame 610 represents a still later point in the breathing cycle of the subject 102. The region 616 is completely filled, and the region 618 is partially filled by inspired respiratory gas. In some embodiments, the regions 616 and 618 may fill at the same rate. The widths of the perfusion regions 620 and 622 are decreased in accordance with the heart rate and the overall size of the graphical element 602 is increased, relative to the frame 608 in accordance with continued inspiration. The frame 612 represents an even later point in the breathing cycle of the subject 102. The region 618 is filled further to a maximum level reached during inspiration and the overall size of the graphical element 602 is increased, relative to the frame 610.

Some embodiments may include an indication (e.g., a line or other shape) that represents the inspiratory volume of a previous breath. In some embodiments, the region 614 may fill first, after which other regions may fill concurrently. Information such as relative fill volume for one or more regions, average volume of one or more previous breaths, average value of one or more previous breaths, and/or other information may be represented by the graphical element 602. In indication of whether a given breath was spontaneous or mechanically provided may also be represented by the graphical element 602 in some embodiments.

Figure 7:
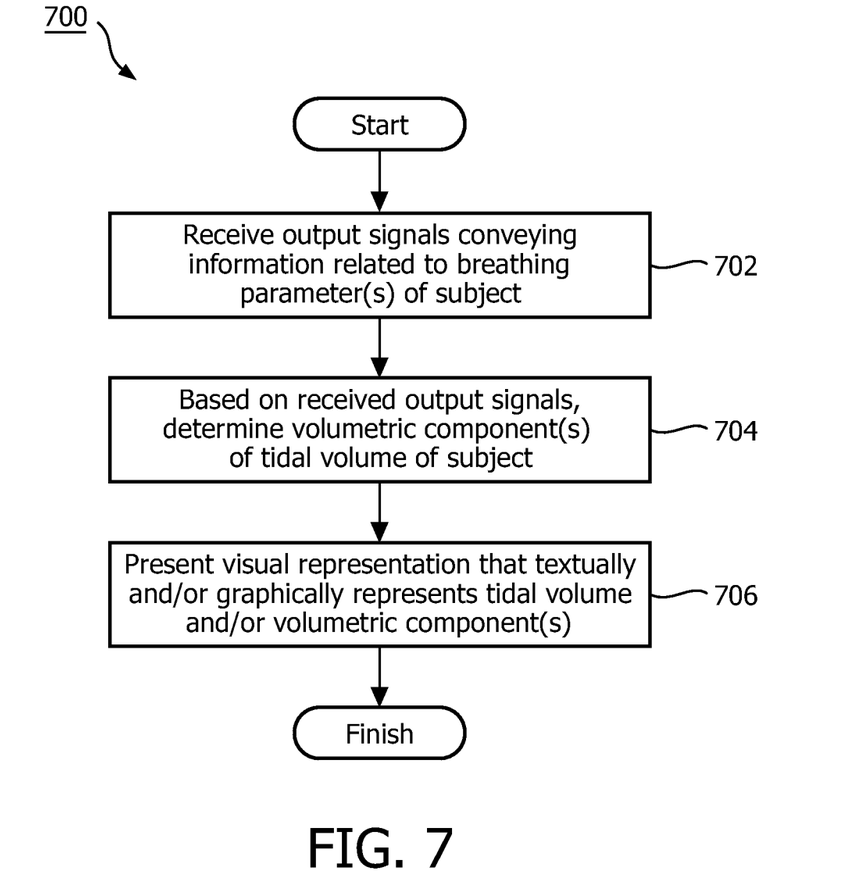
FIG. 7 is a flow chart illustrating an exemplary method for presenting ventilation information.

FIG. 7 is a flow chart illustrating an exemplary method 700 for presenting ventilation information. The operations of the method 700 presented below are intended to be illustrative. In some implementations, the method 700 may be accomplished with one or more additional operations not described, and/or without one or more of the operations discussed. Additionally, the order in which the operations of the method 700 are illustrated in FIG. 7 and described below is not intended to be limiting.

In some implementations, the method 700 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of the method 700 in response to instructions stored electronically on an electronic storage medium. The one or more processing devices may include one or more devices configured through hardware, firmware, and/or software to be specifically designed for execution of one or more of the operations of the method 700.

At an operation 702, output signals are received that convey information related to one or more breathing parameters of a subject being mechanically ventilated. The communications module 130 may be executed to perform the operation 702 in some embodiments.

At an operation 704, based on the received output signals, volumetric components of a tidal volume of the subject are determined. The volumetric components may include an alveolar dead space, an effective alveolar tidal volume, and/or other volumetric components. According to some embodiments, the tidal parameter determination module 132 may be executed to perform the operation 704.

At an operation 706, via a user interface, a visual representation is presented. The visual representation may textually or graphically represent the tidal volume. The visual representation may textually or graphically represent the volumetric components separately from each other. The operation 706 may be performed through execution of the data presentation module 134 in some embodiments.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method for presenting ventilation information with a system including one or more hardware processors configured by machine-readable instructions, a sampling chamber, a sensor, a respiration information interface, and a user interface, the method comprising:

receiving, by a communications module of the one or more hardware processors, output signals from the respiration information interface conveying breathing information related to breathing parameters of a subject being mechanically ventilated, the respiration information interface being configured to receive the breathing information related to the breathing parameters via the sensor, the sensor configured to sense the breathing information related to the breathing parameters within the sampling chamber, the sampling chamber being configured to receive a gas from an airway of the subject;

determining, by a tidal parameter determination module of the one or more hardware processors, based on the received output signals, a tidal volume and volumetric components of the tidal volume of the subject, the volumetric components including an alveolar dead space and an effective alveolar tidal volume, the alveolar dead space being a volume of inspired gas that occupies alveoli but does not take part in oxygen exchange in lungs of the subject, and the effective alveolar tidal volume being a volume of inspired gas that takes part in the oxygen exchange in the lungs of the subject;

presenting, via the user interface, a visual representation pictorially representing at least a portion of a human respiratory system, the visual representation providing an updated ventilation information in an ongoing manner, and the visual representation further providing a textual or a graphical representation of the tidal volume and the volumetric components in a manner which makes an analysis of the tidal volume, the volumetric components and a relationship among the volumetric components intuitive for a user, to enhance a diagnosis and/or treatment of the subject, wherein the visual representation includes a graphical element pictorially outlining an anatomical shape of a lung, wherein the graphical element includes two regions, the two regions being a first region within the outline of the anatomical shape of the lung having a dimension corresponding to the alveolar dead space, and a second region within the outline of the anatomical shape of the lung having a dimension corresponding to the effective alveolar tidal volume, and wherein the two regions of graphical element are presented, via the user interface, with different characteristics;

presenting, via the user interface, a point indicative of effectiveness of the lungs of the subject, the point being where a first perfusion region meets a second perfusion region, the first perfusion region representing deoxygenated blood returning to the lungs of the subject and the second perfusion region representing oxygenated blood that is oxygenated through gas exchange in the lungs of the subject; and shifting, via the user interface, a position of the point based on a condition of the lungs of the subject.

2. The method of claim 1, wherein the visual representation includes a math column textually representing the tidal volume and the volumetric components, the tidal volume and the volumetric components being arranged in the math column with arithmetic operators to convey an arithmetic relationship between the tidal volume and the volumetric components.

3. The method of claim 1, wherein the visual representation includes a stacked bar plot graphically representing the tidal volume and the volumetric components, the stacked bar plot including one or more bars, individual ones of the one or more bars representing the tidal volume at different time intervals and including at least three bar segments stacked from a base line, the at least three bar segments including a first bar segment stacked farthest from a baseline, the first bar segment representing the effective alveolar tidal volume, a second bar segment stacked between the first bar segment and a third bar segment, the second bar segment representing the alveolar dead space, and the third bar segment stacked between the second bar segment and the baseline, the third bar segment representing the airway dead space.

4. The method of claim 1, wherein a dimension of the graphical element as a whole corresponds to the tidal volume, and wherein the graphical element is configured to be animated to change the dimensions of the graphical element and to change the dimensions of the two regions, respectively, during respiration of the subject to reflect a flow of gas into and out of the two regions during respiration.

5. The method of claim 1, wherein the visual representation includes a further graphical element pictorially representing an alveolus shape, a dimension of the further graphical element corresponding to the tidal volume, the further graphical element including further two regions, the further two regions including a further first region having a dimension corresponding to the alveolar dead space, and a further second region having a dimension corresponding to the effective alveolar tidal volume, and the further graphical element being animated to change the dimensions of the further graphical element and the to change the dimensions of the further two regions, respectively, during respiration of the subject to reflect a flow of gas into and out of the at least two regions during respiration.

6. The method of claim 1, wherein the different characteristics of the two regions comprise at least one of a different color, a different shading, a different size and a different position within the graphical element.

7. The method of claim 1, further comprising presenting, via a user interface, multiple visual representations of at least a portion of a same ventilation information, the same ventilation information of each of the multiple visual representations being coordinated in appearance.

8. The method of claim 1, further comprising obtaining, via sensors, blood-gas information and cardiac information, and wherein the graphical element further comprises perfusion regions representing a blood flow through the lungs of the subject.

9. The method of claim 1, further comprising indicating, via the user interface, an indicator representing reference parameters, the reference parameters being at least one of a reference tidal volume and reference values of volumetric components, and the reference parameters being based on at least one of one or more previous breaths and published physiological data.

10. The method of claim 1, wherein the system further comprises a pump, the method further comprising drawing gas with the pump into the sampling chamber.

11. The method of claim 1, wherein the system further comprises a blood gas information interface and a cardiac information interface, the method further comprising:
receiving by the blood gas information interface blood gas parameters of the subject, the blood gas parameters indicating concentrations of molecular species in blood of the subject, the molecular species including one or more of oxygen, carbon dioxide, or bicarbonate, and
receiving by the cardiac information interface cardiac parameters of the subject, the cardiac parameters including one or more of cardiac output, pulmonary capillary blood flow, heart rate, or saturation of peripheral oxygen.

12. A system for presenting ventilation information, the system comprising a sensor, a sampling chamber, a user interface, and one or more hardware processors configured by machine-readable instructions to:
receive output signals conveying breathing information related to one or more breathing parameters of a subject being mechanically ventilated via the sensor configured to sense the breathing information related to the breathing parameters within the sampling chamber, the sampling chamber being configured to receive a gas from an airway of the subject;
determine, based on the received output signals, a tidal volume and volumetric components of a tidal volume of the subject, the volumetric components including an alveolar dead space, and an effective alveolar tidal volume, the alveolar dead space being a volume of inspired gas that occupies alveoli but does not take part in oxygen exchange in lungs of the subject, and the effective alveolar tidal volume being the volume of inspired gas that takes part in oxygen exchange in the lungs of the subject;
facilitate presenting, via the user interface, a visual representation pictorially representing at least a portion of a human respiratory system, the visual representation providing an updated ventilation information in an ongoing manner and the visual representation providing textually or graphically representation of the tidal volume and the volumetric components in a manner which makes an analysis of the tidal volume, the volumetric components and a relationship among the volumetric components intuitive for a user, to enhance a diagnosis and/or treatment of the subject,
wherein the visual representation includes a graphical element pictorially outlining an anatomical shape of a lung,
wherein the graphical element includes two regions, the two regions being a first region within the outline of the anatomical shape of the lung having a dimension corresponding to the alveolar dead space, and a second region within the outline of the anatomical shape of the lung having a dimension corresponding to the effective alveolar tidal volume, and
wherein the two regions of the graphical element are presented, via the user interface, with different characteristics;
facilitate presenting, via the user interface, a point indicative of effectiveness of the lungs of the subject, the point being where a first perfusion region meets a second perfusion region, the first perfusion region representing deoxygenated blood returning to the lungs of the subject and the second perfusion region representing oxygenated blood that is oxygenated through gas exchange in the lungs of the subject; and
facilitate shifting, via the user interface, a position of the point based on a condition of the lungs of the subject.

13. The system of claim 12, wherein the visual representation includes a math column textually representing the tidal volume and the volumetric components, the tidal volume and the volumetric components being arranged in the math column with arithmetic operators to convey an arithmetic relationship between the tidal volume and the volumetric components.

14. The system of claim 12, wherein the visual representation includes a stacked bar plot graphically representing the tidal volume and the volumetric components, the stacked bar plot including one or more bars, individual ones of the one or more bars representing the tidal volume at different time intervals and including at least three bar segments stacked from a base line, the at least three bar segments including a first bar segment stacked farthest from a baseline, the first bar segment representing the effective alveolar tidal volume, a second bar segment stacked between the first bar segment and a third bar segment, the second bar segment representing the alveolar dead space, and the third bar segment stacked between the second bar segment and the baseline, the third bar segment representing the airway dead space.

15. The system of claim 12, wherein a dimension of the graphical element as a whole corresponds to the tidal volume and wherein the graphical element is configured to be animated to change the dimensions of the graphical element and to change the dimensions of the two regions, respectively, during respiration of the subject to reflect a flow of gas into and out of the two regions during respiration.

16. The system of claim 12, wherein the visual representation includes a further graphical element pictorially representing an alveolus shape, a dimension of the further graphical element corresponding to the tidal volume, the further graphical element including further two regions, the further two regions including a further first region having a dimension corresponding to the alveolar dead space, and a further second region having a dimension corresponding to the effective alveolar tidal volume, and the further graphical element being animated to change the dimensions of the further graphical element and to change the dimensions of the further two regions, respectively, during respiration of the subject to reflect a flow of gas into and out of the further two regions during respiration.

17. The system of claim 12, further comprising a pump configured to draw gas into the sampling chamber.

18. The system of claim 12, wherein the one or more hardware processors are further configured by machine-readable instructions to:
receive, by a blood gas information interface, blood gas parameters of the subject, the blood gas parameters indicating concentrations of molecular species in blood of the subject, the molecular species including one or more of oxygen, carbon dioxide, or bicarbonate; and
receive, by a cardiac information interface, cardiac parameters of the subject, the cardiac parameters including one or more of cardiac output, pulmonary capillary blood flow, heart rate, or saturation of peripheral oxygen.

19. A system for presenting ventilation information, the system comprising:
communications means for receiving output signals from a respiration information interface conveying breathing information related to breathing parameters of a subject being mechanically ventilated, the respiration information interface being configured to receive the breathing information related to the breathing parameters via a sensing means configured to sense the breathing information related to the breathing parameters within a sampling chamber, the sampling chamber being configured to receive a gas from an airway of the subject;
tidal parameter determination means for determining, based on the received output signals, a tidal volume and volumetric components of a tidal volume of the subject, the volumetric components including an alveolar dead space, and an effective alveolar tidal volume, the alveolar dead space being a volume of inspired gas that occupies alveoli but does not take part in oxygen exchange in lungs of the subject, and the effective alveolar tidal volume being a volume of inspired gas that takes part in oxygen exchange in the lungs of the subject;
data presentation means for presenting a visual representation pictorially representing a portion of a human respiratory system, the visual representation providing an updated ventilation information in an ongoing manner and the visual representation further providing textually or graphically representation of the tidal volume and the volumetric components and a relationship among the volumetric components intuitive for a user, to enhance a diagnosis and/or treatment of the subject,
wherein the visual representation includes a graphical element pictorially outlining an anatomical shape of a lung,
wherein the graphical element includes two regions, the two regions being a first region having within the anatomical shape of the lung a dimension corresponding to the alveolar dead space, and a second region within the anatomical shape of the lung having a dimension corresponding to the effective alveolar tidal volume, and
wherein the two regions of the graphical element are presented, via a user interface, with different characteristics;
data presentation means for presenting a point indicative of effectiveness of the lungs of the subject, the point being where a first perfusion region meets a second perfusion region, the first perfusion region representing deoxygenated blood returning to the lungs of the subject and the second perfusion region representing oxygenated blood that is oxygenated through gas exchange in the lungs of the subject; and
data presentation means for shifting a position of the point based on a condition of the lungs of the subject.

20. The system of claim 19, wherein the visual representation includes a math column textually representing the tidal volume and the volumetric components, the tidal volume and the volumetric components being arranged in the math column with arithmetic operators to convey an arithmetic relationship between the tidal volume and the volumetric components.

21. The system of claim 19, wherein the visual representation includes a stacked bar plot graphically representing the tidal volume and the volumetric components, the stacked bar plot including one or more bars, individual ones of the one or more bars representing the tidal volume at different time intervals and including at least three bar segments stacked from a base line, the at least three bar segments including a first bar segment stacked farthest from a baseline, the first bar segment representing the effective alveolar tidal volume, a second bar segment stacked between the first bar segment and a third bar segment, the second bar segment representing the alveolar dead space, and the third bar segment stacked between the second bar segment and the baseline, the third bar segment representing the airway dead space.

22. The system of claim 19, wherein a dimension of the graphical element as a whole corresponds to the tidal volume and wherein the graphical element is configured to be animated to change the dimensions of the graphical element and to change the dimensions of the two regions, respectively, during respiration of the subject to reflect a flow of gas into and out of the two regions during respiration.

23. The system of claim 19, wherein the visual representation includes a further graphical element pictorially representing an alveolus shape, a dimension of the further graphical element corresponding to the tidal volume, the further graphical element including further two regions, the further two regions including a further first region having a dimension corresponding to the alveolar dead space, and a further second region having a dimension corresponding to the effective alveolar tidal volume, and the further graphical element being animated to change the dimensions of the further graphical element and to change the dimensions of the further two regions, respectively, during respiration of the subject to reflect a flow of gas into and out of the further two regions during respiration.

24. The system of claim 19, further comprising a means for drawing gas into the sampling chamber.

\* \* \* \* \*